US011759095B2

(12) United States Patent
Chung

(10) Patent No.: US 11,759,095 B2
(45) Date of Patent: Sep. 19, 2023

(54) IMAGE CAPTURING ASSEMBLY AND RELATED ENDOSCOPE

(71) Applicant: ALTEK BIOTECHNOLOGY CORPORATION, Hsinchu (TW)

(72) Inventor: Te-Yu Chung, Hsinchu (TW)

(73) Assignee: ALTEK BIOTECHNOLOGY CORPORATION, Hsinchu (TW)

( * ) Notice: Subject to any disclaimer, the term of this patent is extended or adjusted under 35 U.S.C. 154(b) by 0 days.

(21) Appl. No.: 17/460,282

(22) Filed: Aug. 29, 2021

(65) Prior Publication Data

US 2023/0067547 A1 Mar. 2, 2023

(51) Int. Cl.
*A61B 1/05* (2006.01)
*A61B 1/00* (2006.01)

(52) U.S. Cl.
CPC .......... *A61B 1/051* (2013.01); *A61B 1/00096* (2013.01)

(58) Field of Classification Search
CPC ....... A61B 1/00096; A61B 1/05; A61B 1/051; G02B 23/2484; H04N 5/2253; H04N 5/2254; H04N 5/22541; H04N 23/55; H04N 23/555; H05K 1/183; H05K 3/3465; H05K 3/366; H05K 2201/044; H05K 2201/046; H05K 2201/048; H05K 2201/049; H05K 2201/09036; H05K 2201/09954; H05K 2201/10121; H05K 2201/10151
See application file for complete search history.

(56) References Cited

U.S. PATENT DOCUMENTS

| | | | | |
|---|---|---|---|---|
| 5,040,069 A * | 8/1991 | Matsumoto | .......... | H04N 5/2253 348/340 |
| 5,365,268 A * | 11/1994 | Minami | ................. | H04N 23/54 257/E31.118 |
| 6,567,115 B1 * | 5/2003 | Miyashita | ............... | A61B 1/051 348/76 |
| 2009/0268019 A1 * | 10/2009 | Ishii | ....................... | G03B 17/02 348/294 |
| 2009/0306475 A1 * | 12/2009 | Yamamoto | ........... | H05K 1/0243 600/110 |

(Continued)

FOREIGN PATENT DOCUMENTS

CN 102854595 A 1/2013
CN 104434001 A 3/2015

(Continued)

*Primary Examiner* — Michael J Carey
*Assistant Examiner* — Stephen Floyd London
(74) *Attorney, Agent, or Firm* — Winston Hsu

(57) ABSTRACT

An image capturing assembly is provided and includes a fixture, a lens assembly, an image sensing device and a circuit board. The fixture includes a fixture body and at least one first contact. An accommodating space is formed on the fixture body. The at least one first contact is disposed on the fixture body. The lens assembly is engaged with the fixture body. The image sensing device is disposed inside the accommodating space. The image sensing device includes at least one second contact electrically connected to the at least one first contact. The circuit board includes a board body and at least one third contact. The board body is perpendicular to and affixed with the fixture body. The at least one third contact is disposed on the board body and electrically connected to the at least one first contact. Besides, a related endoscope is further provided.

20 Claims, 17 Drawing Sheets

(56) References Cited

U.S. PATENT DOCUMENTS

| | | | |
|---|---|---|---|
| 2014/0078280 A1* | 3/2014 | Yoshida | A61B 1/00163 |
| | | | 348/76 |
| 2016/0072989 A1* | 3/2016 | Kennedy | A61B 1/051 |
| | | | 348/76 |
| 2017/0035279 A1* | 2/2017 | Fujii | A61B 1/051 |
| 2017/0064164 A1* | 3/2017 | Nishihara | A61B 1/005 |
| 2017/0064249 A1* | 3/2017 | Kitano | A61B 1/051 |
| 2018/0041670 A1* | 2/2018 | Fujimori | H01L 27/14636 |
| 2018/0070803 A1* | 3/2018 | Mikami | A61B 1/051 |
| 2019/0021581 A1* | 1/2019 | Ishizuka | A61B 1/051 |
| 2019/0133423 A1* | 5/2019 | Birnkrant | A61B 1/051 |
| 2020/0110257 A1* | 4/2020 | Motohara | G02B 23/2446 |
| 2021/0249393 A1* | 8/2021 | Wu | A61B 1/0011 |

FOREIGN PATENT DOCUMENTS

| | | |
|---|---|---|
| CN | 102466844 B | 8/2016 |
| CN | 113951803 A | 1/2022 |
| KR | 10-2018-0117306 A | 10/2018 |
| WO | 2019/193911 A1 | 10/2019 |
| WO | 2019/207650 A1 | 10/2019 |

\* cited by examiner

IMAGE CAPTURING ASSEMBLY AND RELATED ENDOSCOPE

BACKGROUND OF THE INVENTION

1. Field of the Invention

The present invention relates to an image capturing assembly and a related endoscope, and more specifically, to an image capturing assembly with compact structure and small size, and a related endoscope.

2. Description of the Prior Art

An endoscopy is a medical procedure in which an endoscope is inserted into a patient's body to allow a surgeon to inspect an interior of the patient's body. The endoscopy has gained broad acceptance because it only needs a small incision for insertion of the endoscope. However, since the conventional endoscope still has a bulky image capturing assembly, a size of the incision cannot be further reduced in order for insertion of the endoscope with such a bulky image capturing assembly. Therefore, an improvement is required.

SUMMARY OF THE INVENTION

It is an objective of the present invention to provide an image capturing assembly with compact structure and small size, and a related endoscope for solving the aforementioned problem.

In order to achieve the aforementioned objective, the present invention discloses an image capturing assembly used in an endoscope. The image capturing assembly includes a fixture, a lens assembly, an image sensing device and a circuit board. The fixture includes a fixture body and at least one first contact. An accommodating space is formed on the fixture body. The at least one first contact is disposed on the fixture body. The lens assembly is engaged with the fixture body. The image sensing device is disposed inside the accommodating space. The image sensing device includes at least one second contact electrically connected to the at least one first contact. The circuit board includes a board body and at least one third contact. The board body is perpendicular to and affixed with the fixture body. The at least one third contact is disposed on the board body and electrically connected to the at least one first contact.

In order to achieve the aforementioned objective, the present invention further discloses an endoscope. The endoscope includes an insertion tube and the aforementioned image capturing assembly. The image capturing assembly is connected to the insertion tube.

In summary, in the present invention, the fixture body of the fixture is perpendicular to and affixed with the board body of the circuit board. Furthermore, the image sensing device is disposed inside the accommodating space formed on the fixture body, and the second contact of the image sensing device is electrically connected to the third contact of circuit board by the first contact of the fixture. The aforementioned configuration of the present invention has a space-saving arrangement. Therefore, the present invention has advantages of compact structure and small size.

These and other objectives of the present invention will no doubt become obvious to those of ordinary skill in the art after reading the following detailed description of the preferred embodiment that is illustrated in the various figures and drawings.

DETAILED DESCRIPTION

In the following detailed description of the preferred embodiments, reference is made to the accompanying drawings which form a part hereof, and in which is shown by way of illustration specific embodiments in which the invention may be practiced. In this regard, directional terminology, such as "top", "bottom", "front", "back", etc., is used with reference to the orientation of the Figure (s) being described. The components of the present invention can be positioned in a number of different orientations. As such, the directional terminology is used for purposes of illustration and is in no way limiting. Accordingly, the drawings and descriptions will be regarded as illustrative in nature and not as restrictive. Also, the term "connect" is intended to mean either an indirect or direct electrical/mechanical connection. Thus, if a first device is connected to a second device, that connection may be through a direct electrical/mechanical connection, or through an indirect electrical/mechanical connection via other devices and connections.

Figure 1:
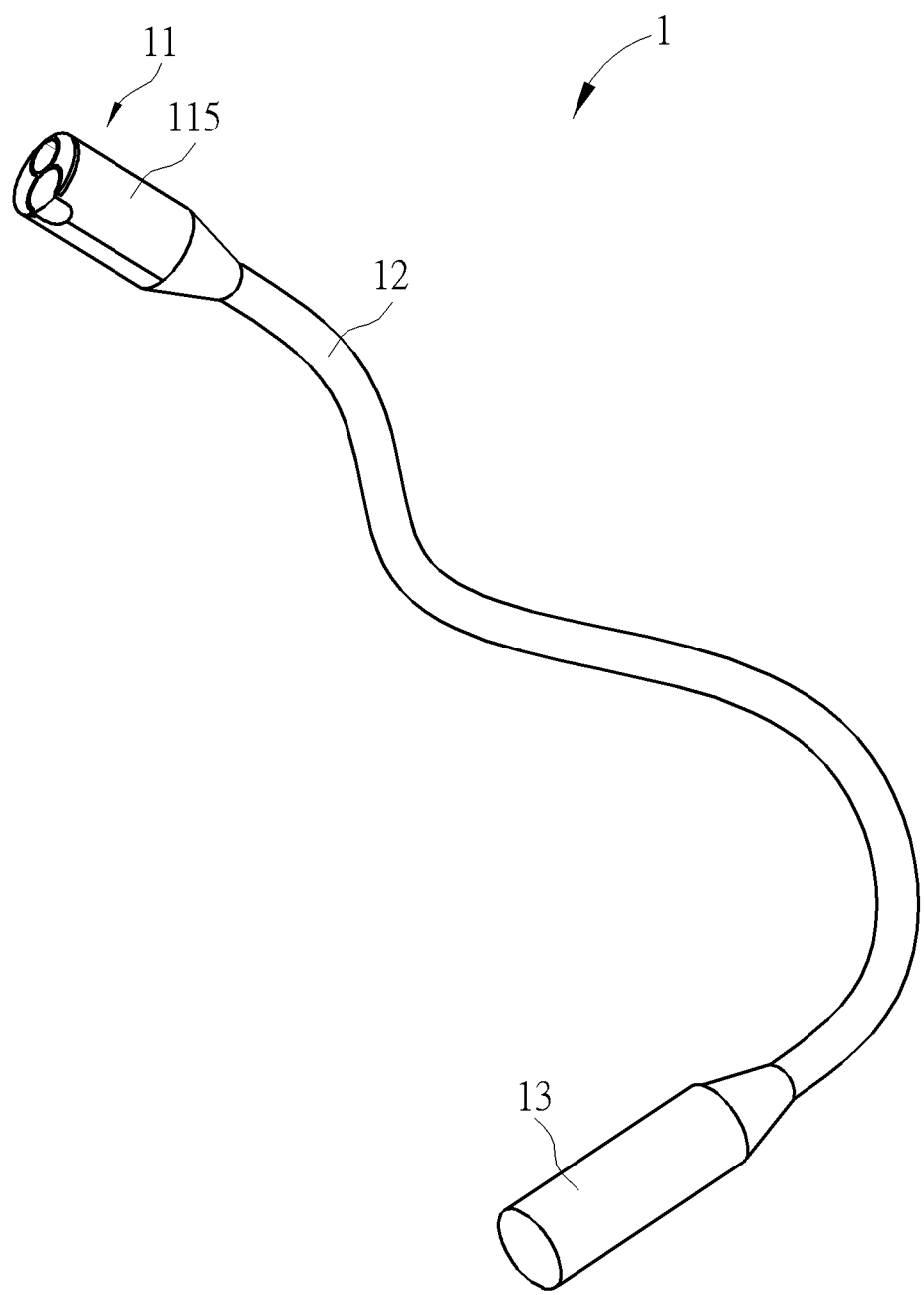
FIG. 1 is a schematic diagram of an endoscope according to a first embodiment of the present invention.

Please refer to FIG. 1. FIG. 1 is a schematic diagram of an endoscope 1 according to a first embodiment of the present invention. As shown in FIG. 1, the endoscope 1 includes an image capturing assembly 11, an insertion tube 12 and a handle 13. The image capturing assembly 11 is for capturing images an interior of a patient's body. The handle 13 is for hand-holding and can be provided with a control console for at least controlling the image capturing assembly 11. The insertion tube 12 is connected between the image capturing assembly 11 and the handle 13. In operation, the insertion tube 12 is suitable for inserting into the interior lumen, so that the image capturing assembly 11 captures images of an internal organ or tissue in detail. In addition, the stiffness of the insertion tube 12 may be variable for different usages, and the present invention is not limited to flexible endoscope.

Figure 2:
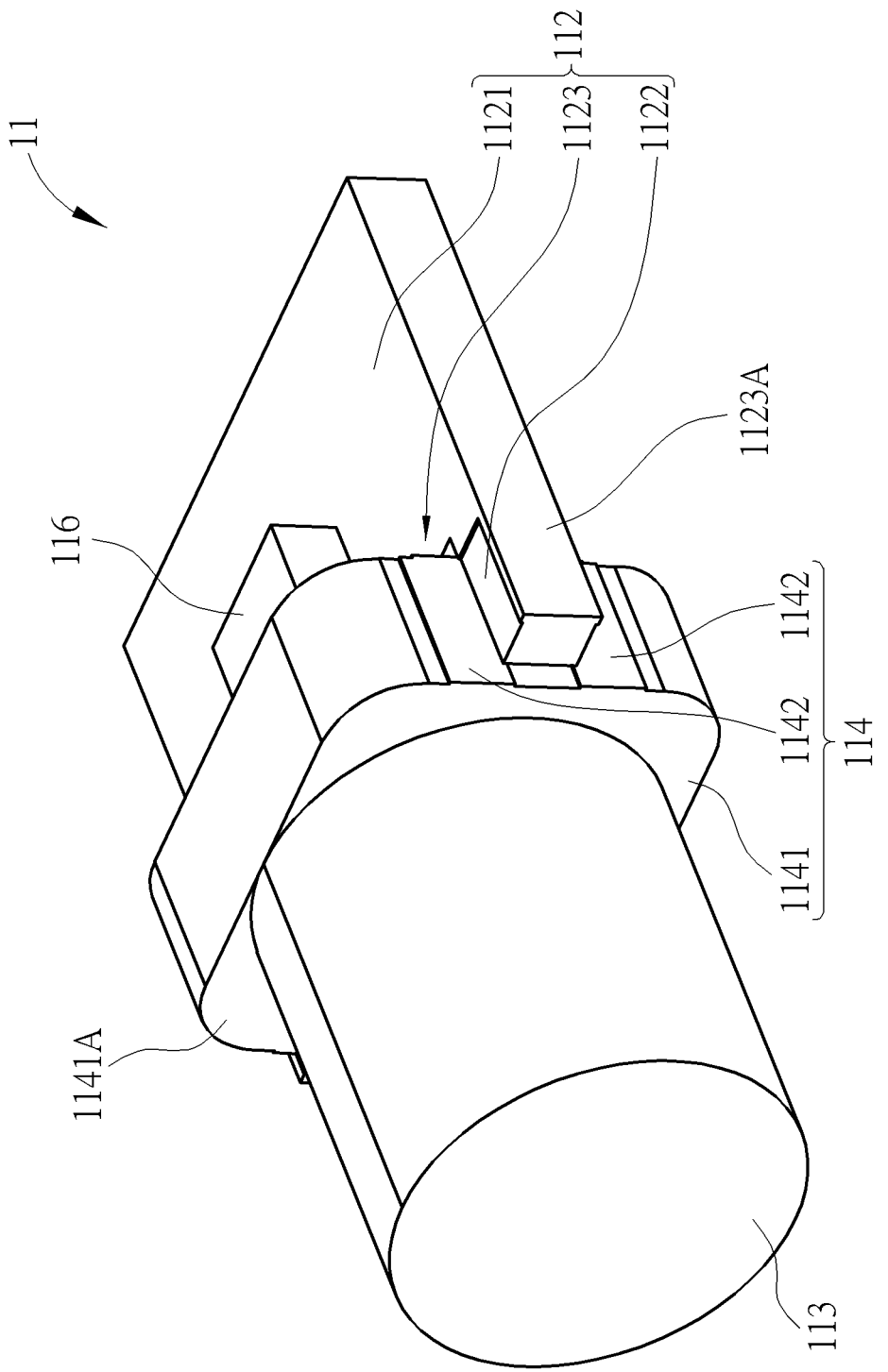
FIG. 2 and FIG. 3 are partial diagrams of the image capturing assembly at different views according to the first embodiment of the present invention.
Figure 3:
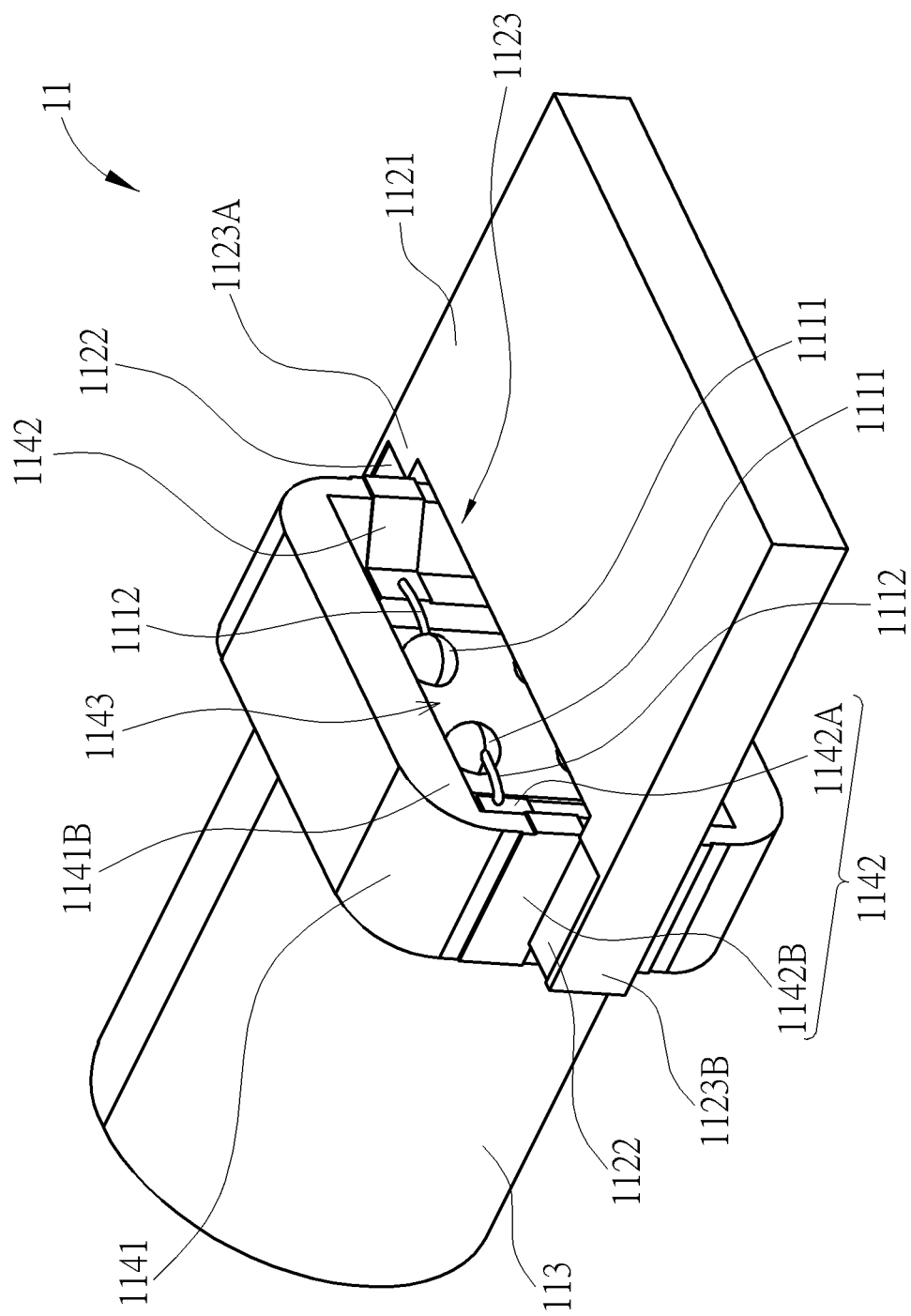
Figure 4:
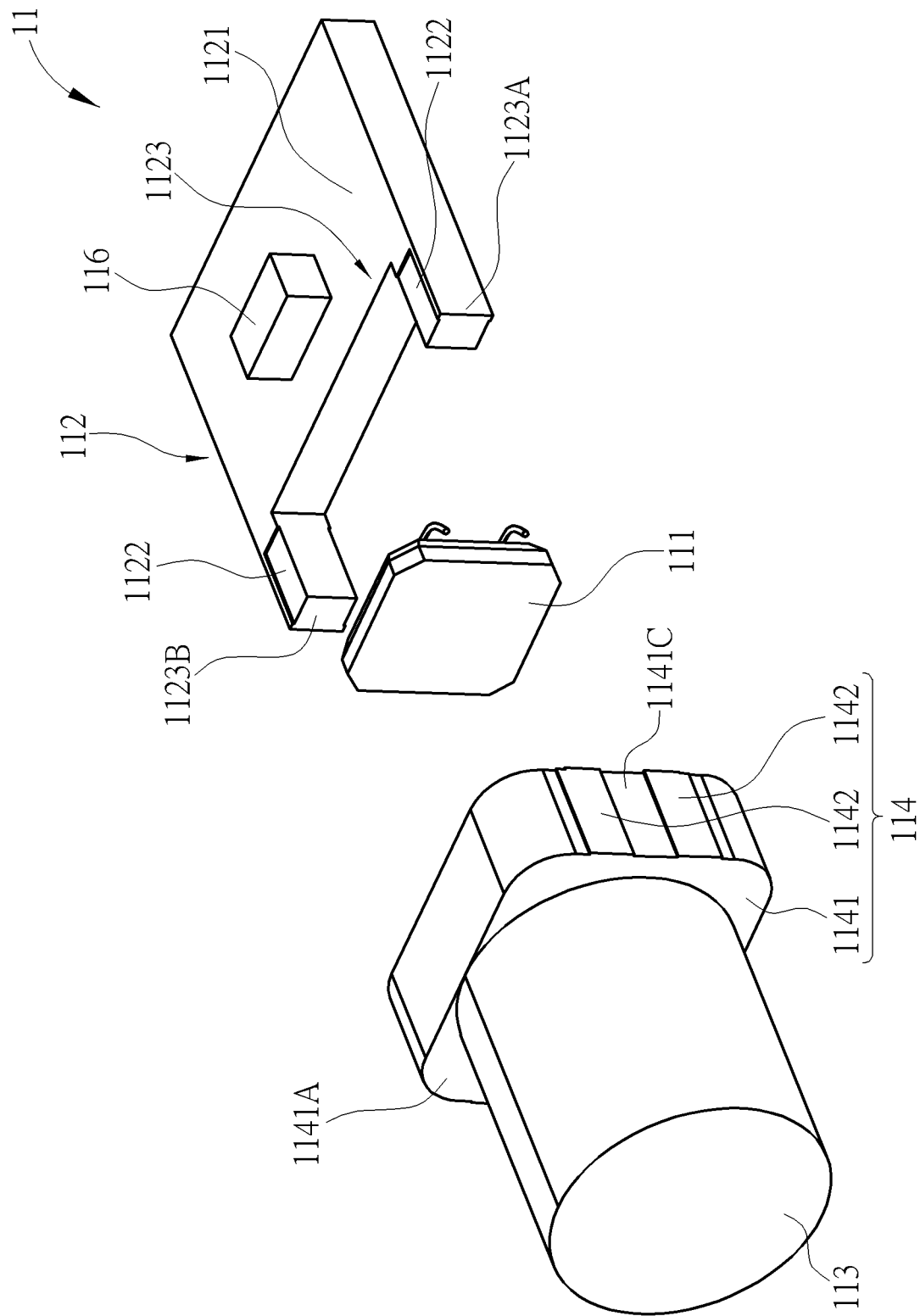
FIGS. 4 and 5 are partial exploded diagrams of the image capturing assembly at different views according to the first embodiment of the present invention.
Figure 5:
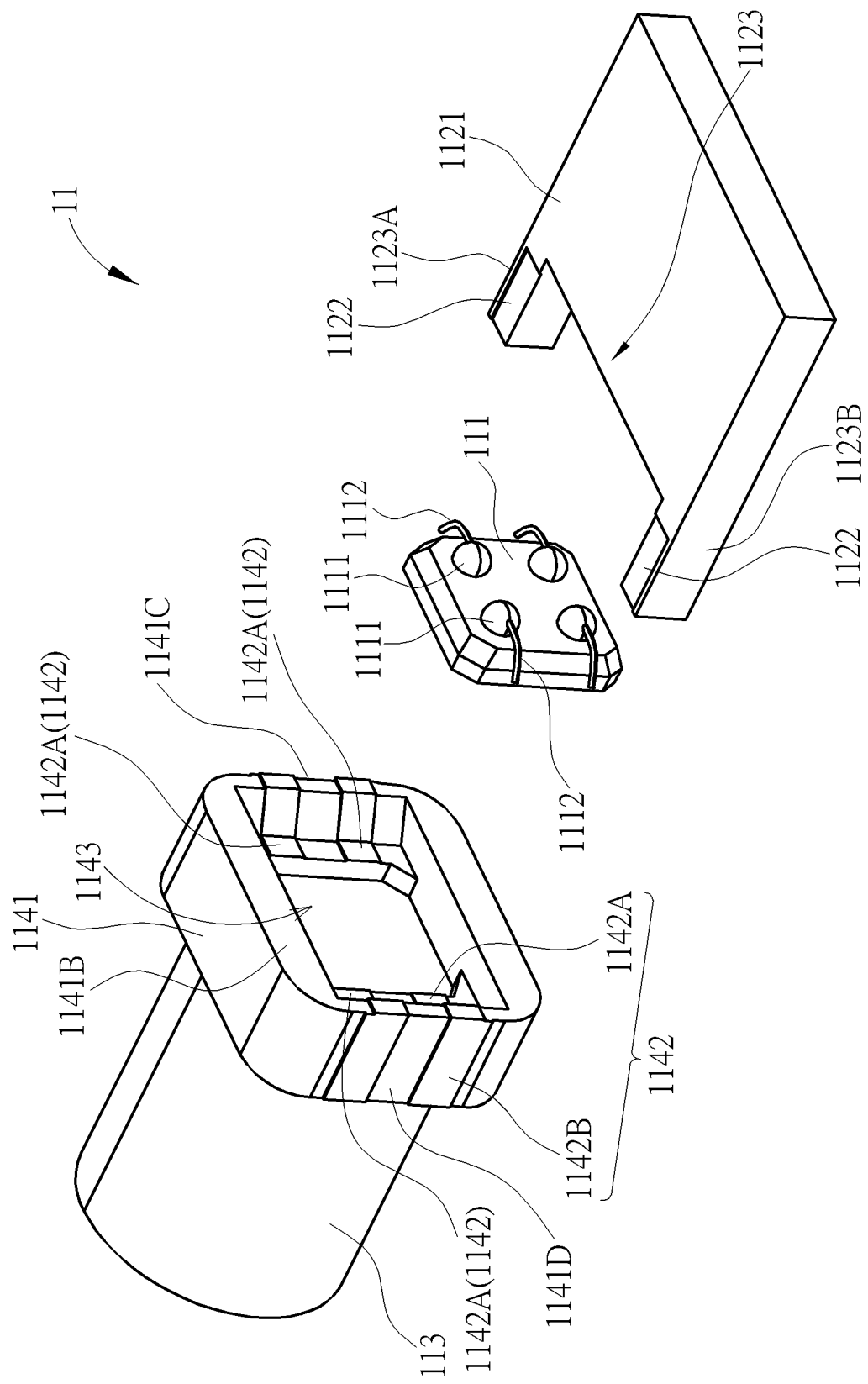

Please refer to FIG. 1 to FIG. 5. FIG. 2 and FIG. 3 are partial diagrams of the image capturing assembly 11 at different views according to the first embodiment of the present invention. FIGS. 4 and 5 are partial exploded diagrams of the image capturing assembly 11 at different views according to the first embodiment of the present invention. As shown in FIG. 1 to FIG. 5, the image capturing assembly 11 is located at a distal end of the insertion tube 12 away from the handle 13 and includes an image sensing device 111, a circuit board 112, a lens assembly 113, a fixture 114 and a housing 115.

The image sensing device 111, the circuit board 112, the lens assembly 113 and the fixture 114 are disposed inside the housing 115. The circuit board 112 can be electrically connected to the control console of the handle 13 by at least one cable, which is not shown in the figures. The fixture 114 is configured to position the lens assembly 113 and includes a fixture body 1141 and four first contacts 1142. An accommodating space 1143 is formed on the fixture body 1141. The four first contacts 1142 are disposed on the fixture body 1141. The lens assembly 113 is engaged with the fixture body 1141 and can be a fixed focal length lens assembly or a zoom lens assembly configured to zoom in or zoom out a view of the image sensing device 111. The image sensing device 111 is disposed inside the accommodating space 1143 and can be, e.g., a CMOS sensor. The image sensing device 111 includes four second contacts 1111 electrically connected to the four first contacts 1142 respectively.

The circuit board 112 includes a board body 1121 and four third contacts 1122. The board body 1121 is perpendicular to and affixed with the fixture body 1141. The four third contacts 1122 are disposed on the board body 1121 and electrically connected to the four first contacts 1142, so that the four second contacts 1111 can be electrically connected to the four third contacts 1122 by the four first contacts 1142 respectively.

However, the numbers of the first contact, the second contact and the third contact are not limited to this embodiment. For example, in another embodiment, there can be only two first contacts, two second contacts and two third contacts.

Besides, as shown in FIG. 2 and FIG. 4, the image capturing assembly 11 further includes a passive electronic component 116, e.g., a capacitor or a resistor, disposed on a side of the circuit board 112.

However, the present invention is not limited to this embodiment. For example, in anther embodiment, there can be no passive electronic component or two passive electronic components located at a same side or two opposite sides of the circuit board.

Specifically, as shown in FIG. 2 to FIG. 5, the lens assembly 113 is fixedly engaged with a first side 1141A of the fixture body 1141. The accommodating space 1143 is formed on a second side 1141B of the fixture body 1141 away from the lens assembly 113 and adjacent to the board body 1121. The image sensing device 111 is positioned between the fixture body 1141 and the board body 1121 when the image sensing device 111 is disposed inside the accommodating space 1143. A notch 1123 is formed on the board body 1121. The fixture body 1141 is engaged with the notch 1123. Each of the third contacts 1122 is located adjacent to an outer periphery of the notch 1123. An optical axis of the lens assembly 113 is perpendicular to an opening of the accommodating space 1143 and parallel to the circuit board 112, i.e., an extending direction of the lens assembly 113 is parallel to a normal direction of the second side 1141B of the fixture body 1141 and perpendicular to a normal direction of the board body 1121.

Each of the first contacts 1142 includes a first portion 1142A and a second portion 1142B electrically connected to the first portion 1142A. Each of the first portions 1142A is disposed on a wall of the fixture body 1141 adjacent to the accommodating space 1143 and electrically connected to the corresponding second contact 1111, and each of the second portions 1142B is disposed on a wall of the fixture body 1141 adjacent to the outer periphery of the notch 1123 and electrically connected to the corresponding third contact 1122.

More specifically, as shown in FIG. 2 to FIG. 5, the second portions 1142B of two of the first contacts 1142 are located at a first lateral side 1141C of the fixture body 1141 and spaced apart from and aligned with each other along an up-down direction perpendicular to the circuit board 112, and the other two second portions 1142B of the other two of the first contacts 1142 are located at a second lateral side 1141D of the fixture body 1141 opposite to the first lateral side 1141C of the fixture body 1141 and spaced apart from and aligned with each other along the up-down direction perpendicular to the circuit board 112.

The notch 1123 includes a first lateral portion 1123A and a second lateral portion 1123B located at two opposite lateral sides of the circuit board 112 respectively. When the fixture body 1141 is engaged with the notch 1123, the first lateral portion 1123A is located adjacent to the first lateral side 1141C of the fixture body 1141 and between the second portions 1142B of the two of the first contacts 1142 located at the first lateral side 1141C of the fixture body 1141, and the second lateral portion 1123B is located adjacent to the second lateral side 1141D of the fixture body 1141D and between the other two second portions 1142B of the other two of the first contacts 1142 located at the second lateral side 1141D of the fixture body 1141.

Two of the third contacts 1122 are disposed on a top side and a bottom side of the first lateral portion 1123A respectively, and the other two of the third contacts 1122 are disposed on a top side and a bottom side of the second lateral portion 1123B respectively. Along the up-down direction perpendicular to the circuit board 112, the projections of the third contacts 1122 disposed on the top side respectively overlap with the projections of the third contacts 1122 disposed on the bottom side.

Each of the third contacts 1122 is perpendicular to the second portion 1142B of the corresponding first contact 1142 and can be affixed with and electrically connected to the second portion 1142B of the corresponding first contact 1142 by a corresponding solder structure, which is not shown in the figures. Each of the second contacts 1111 is a soldering ball electrically connected to the corresponding first portion 1142A of the corresponding first contact 1142 by wire bonding technology with a corresponding wire 1112. That is, each of the second contacts 1111 is electrically connected to the corresponding third contact 1122 via the corresponding first contact 1142.

However, the present invention is not limited to this embodiment. For example, in another embodiment, each of the second contacts can be a protruding pin or a flat pad electrically connected to the corresponding first contact by a soldering structure. Alternatively, in another embodiment, each of the third contacts can be electrically connected to the second portion of the corresponding first contact by a wire.

The aforementioned configuration of the first embodiment the present invention has a space-saving arrangement. Therefore, the present invention has advantages of compact structure and small size.

Figure 6:
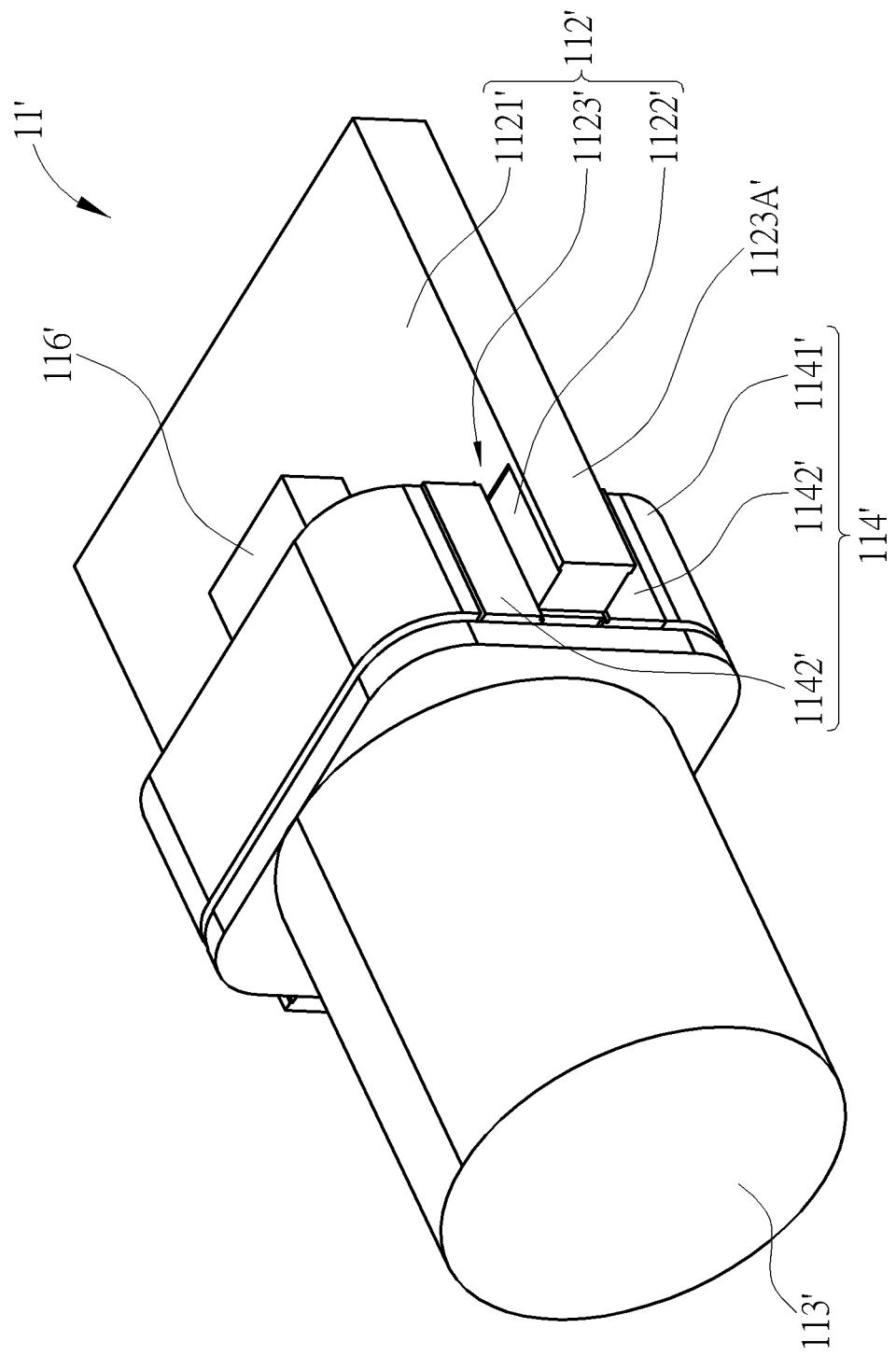
FIG. 6 and FIG. 7 are partial diagrams of an image capturing assembly at different views according to a second embodiment of the present invention.
Figure 7:
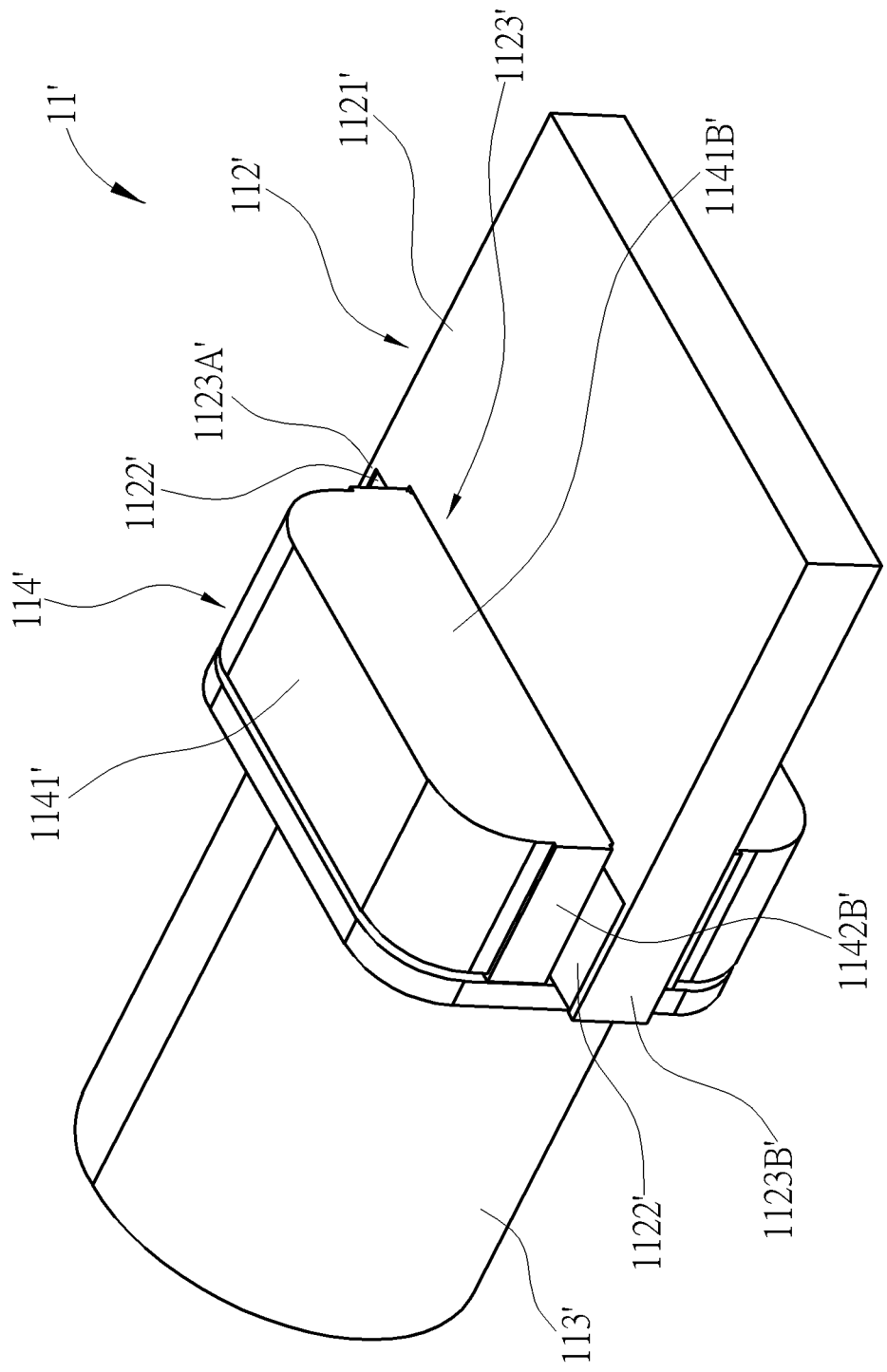
Figure 8:
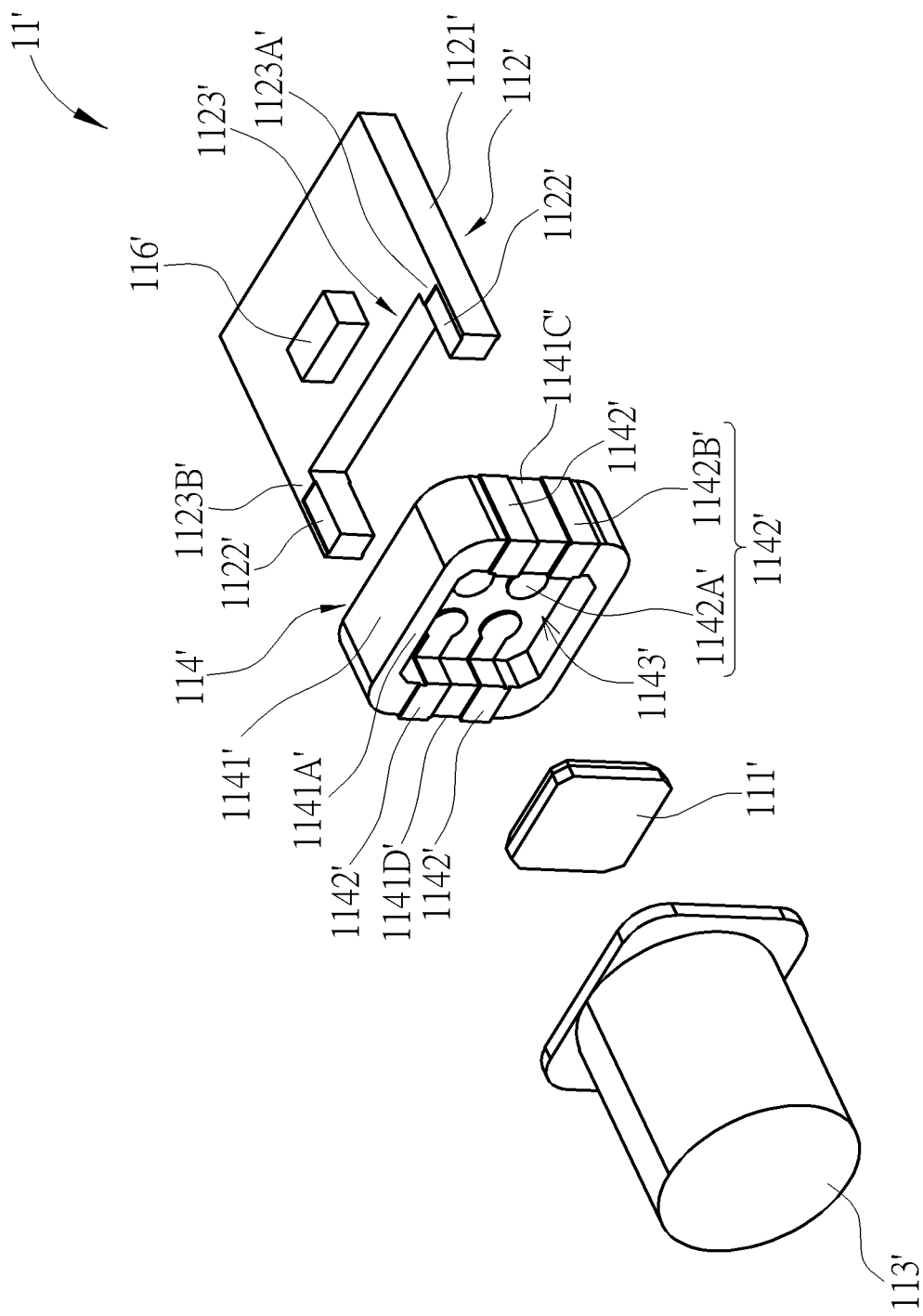
FIGS. 8 and 9 are partial exploded diagrams of the image capturing assembly at different views according to the second embodiment of the present invention.
Figure 9:
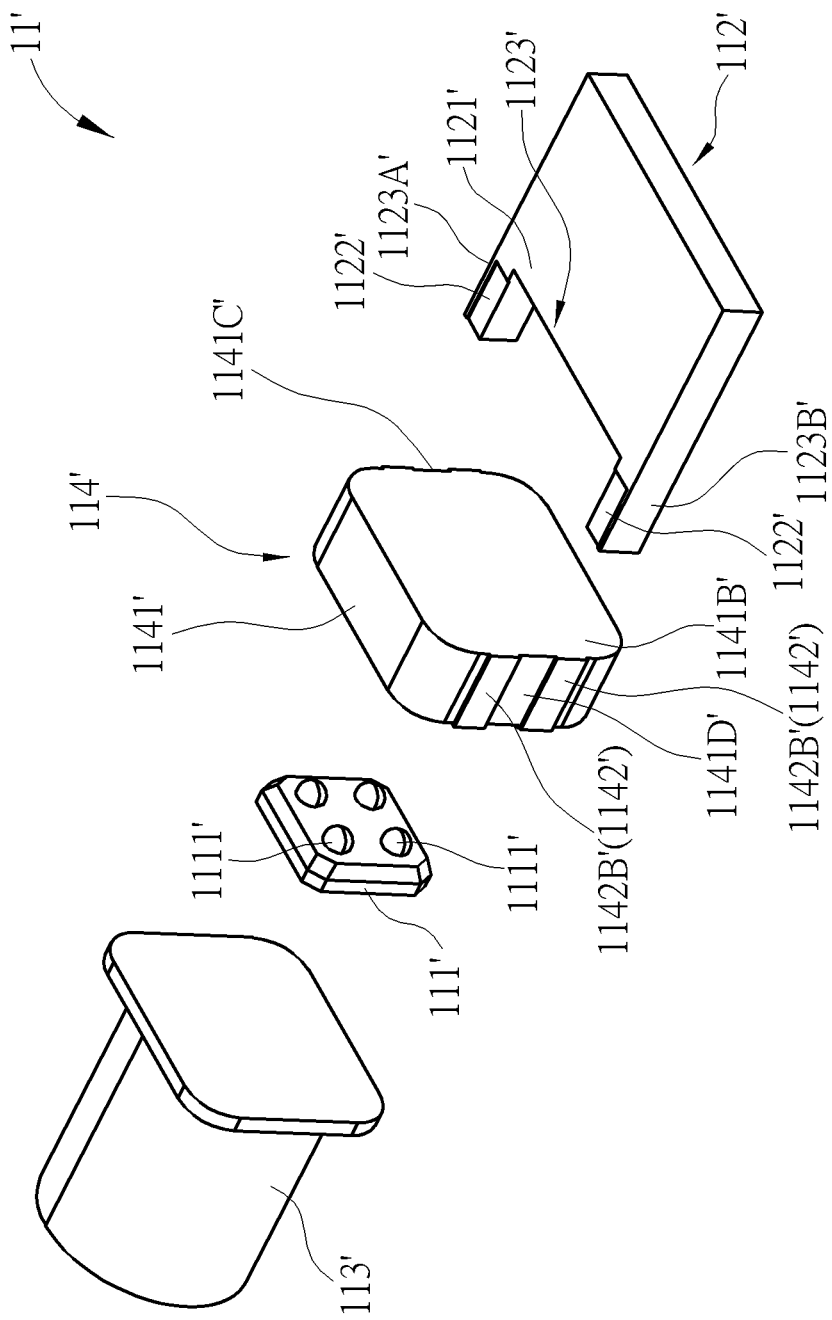

Please refer to FIG. 6 to FIG. 9. FIG. 6 and FIG. 7 are partial diagrams of an image capturing assembly 11' at different views according to a second embodiment of the present invention. FIGS. 8 and 9 are partial exploded diagrams of the image capturing assembly 11' at different views according to the second embodiment of the present invention. The image capturing assembly 11' of this embodiment includes an image sensing device 111', a circuit board 112', a lens assembly 113', a fixture 114' and a passive electronic component 116'. The lens assembly 113' is detachably engaged with a first side 1141A' of a fixture body 1141' of the fixture 114' away from a board body 1121' of the circuit board 112' and adjacent to the lens assembly 113'. An optical axis of the lens assembly 113' is perpendicular to the first side 1141A' of the fixture 114' and parallel to the circuit board 112', i.e., an extending direction of the lens assembly 113' is parallel to a normal direction of the first side 1141A' of the fixture body 1141' and perpendicular to a normal direction of the board body 1121'.

As shown in FIG. 6 to FIG. 9, different from the first embodiment, an accommodating space 1143' is formed on the first side 1141A' of the fixture body 1141' away from the board body 1121' of the circuit board 112' and adjacent to the lens assembly 113', and the image sensing device 111' is positioned between the fixture body 1141' and the lens assembly 113' when the image sensing device 111' is disposed inside the accommodating space 1143'. Each of second contacts 1111' of the image sensing device 111' is electrically connected to a first portion 1142A' of a corresponding first contact 1142' of the fixture body 114' by surface mount technology. Other details of this embodiment are similar to the ones of the first embodiment. Detailed description is omitted herein for simplicity.

Figure 10:
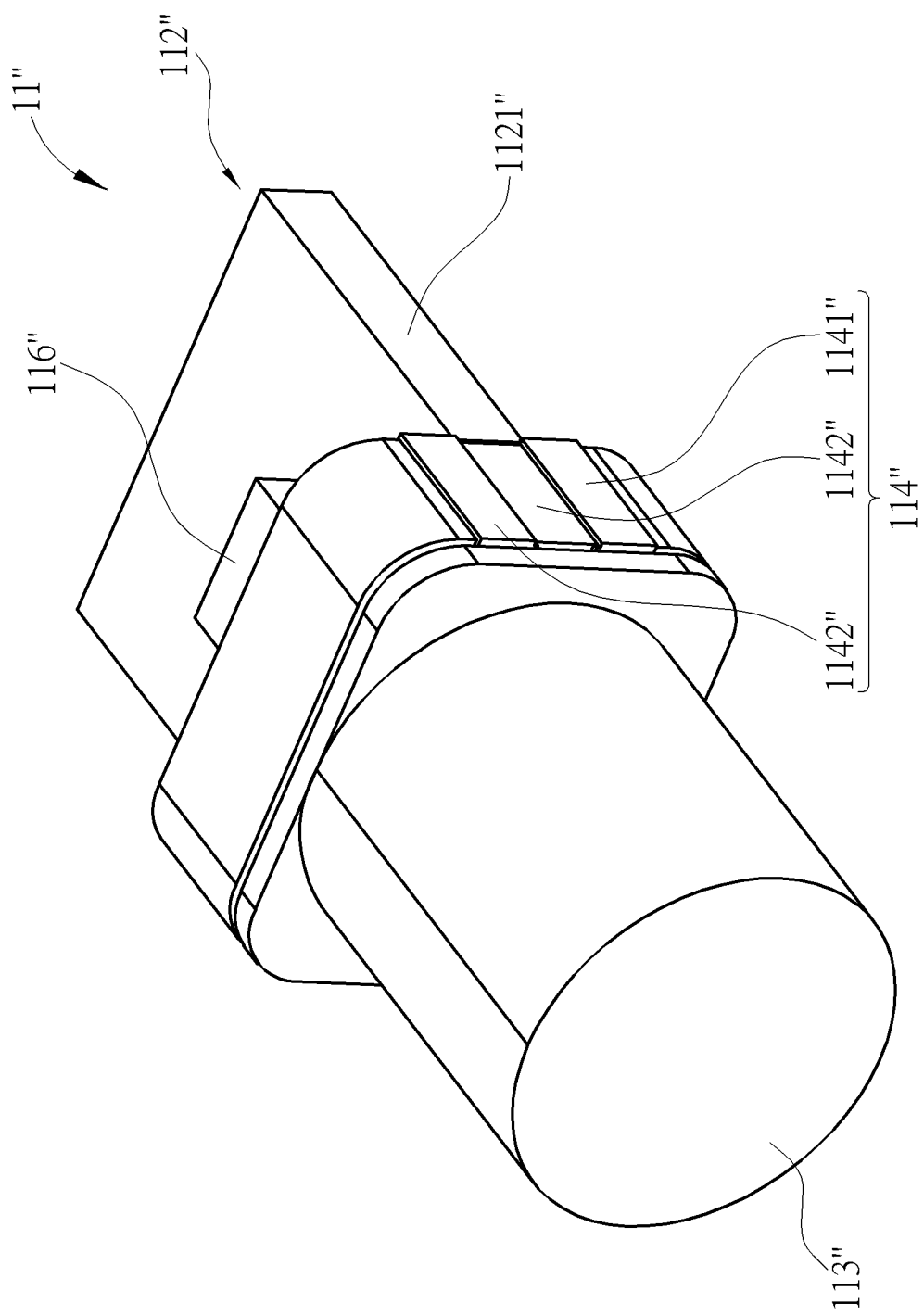
FIG. 10 and FIG. 11 are partial diagrams of an image capturing assembly at different views according to a third embodiment of the present invention.
Figure 11:
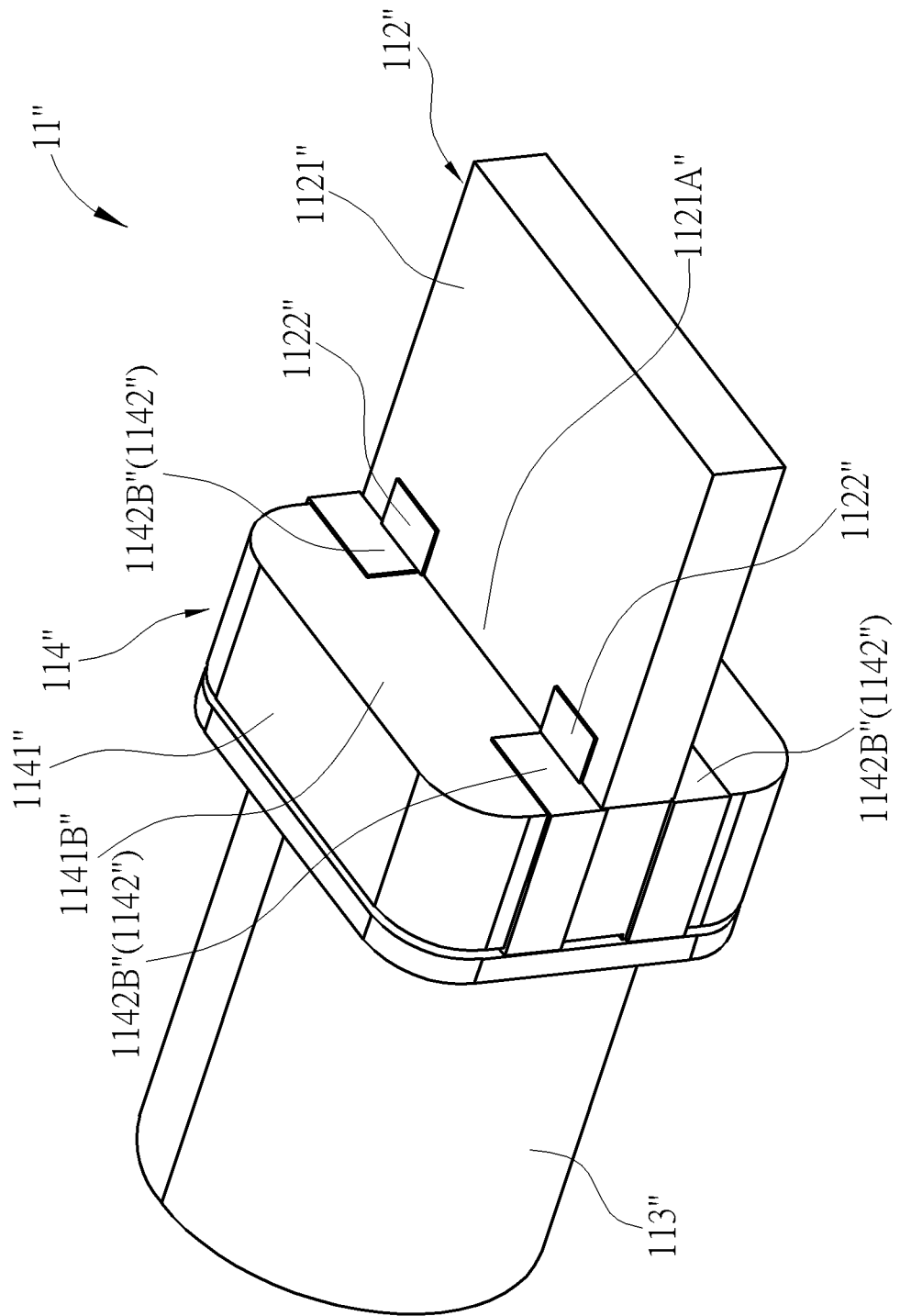
Figure 12:
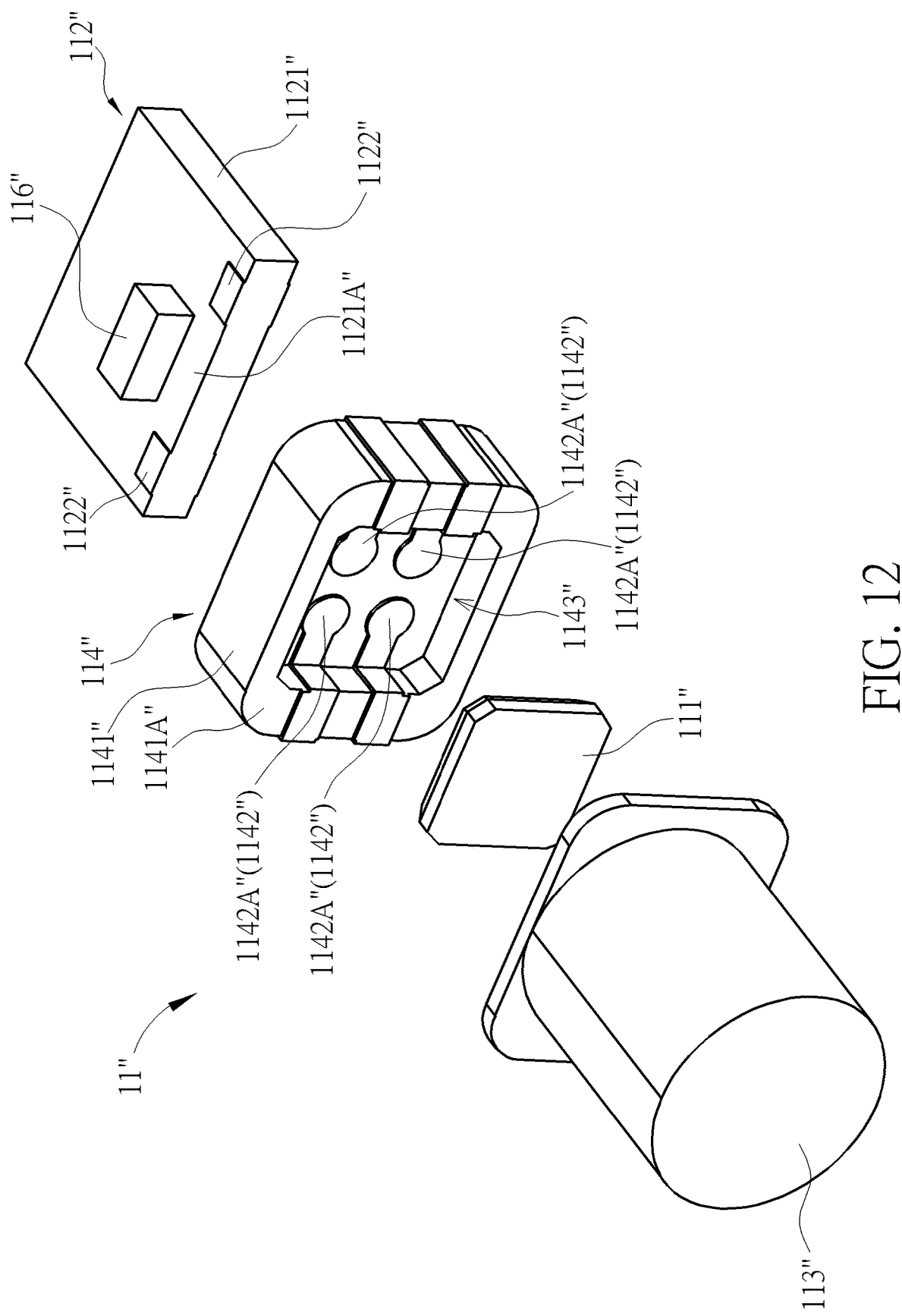
FIG. 12 and FIG. 13 are partial exploded diagrams of the image capturing assembly at different views according to the third embodiment of the present invention.
Figure 13:
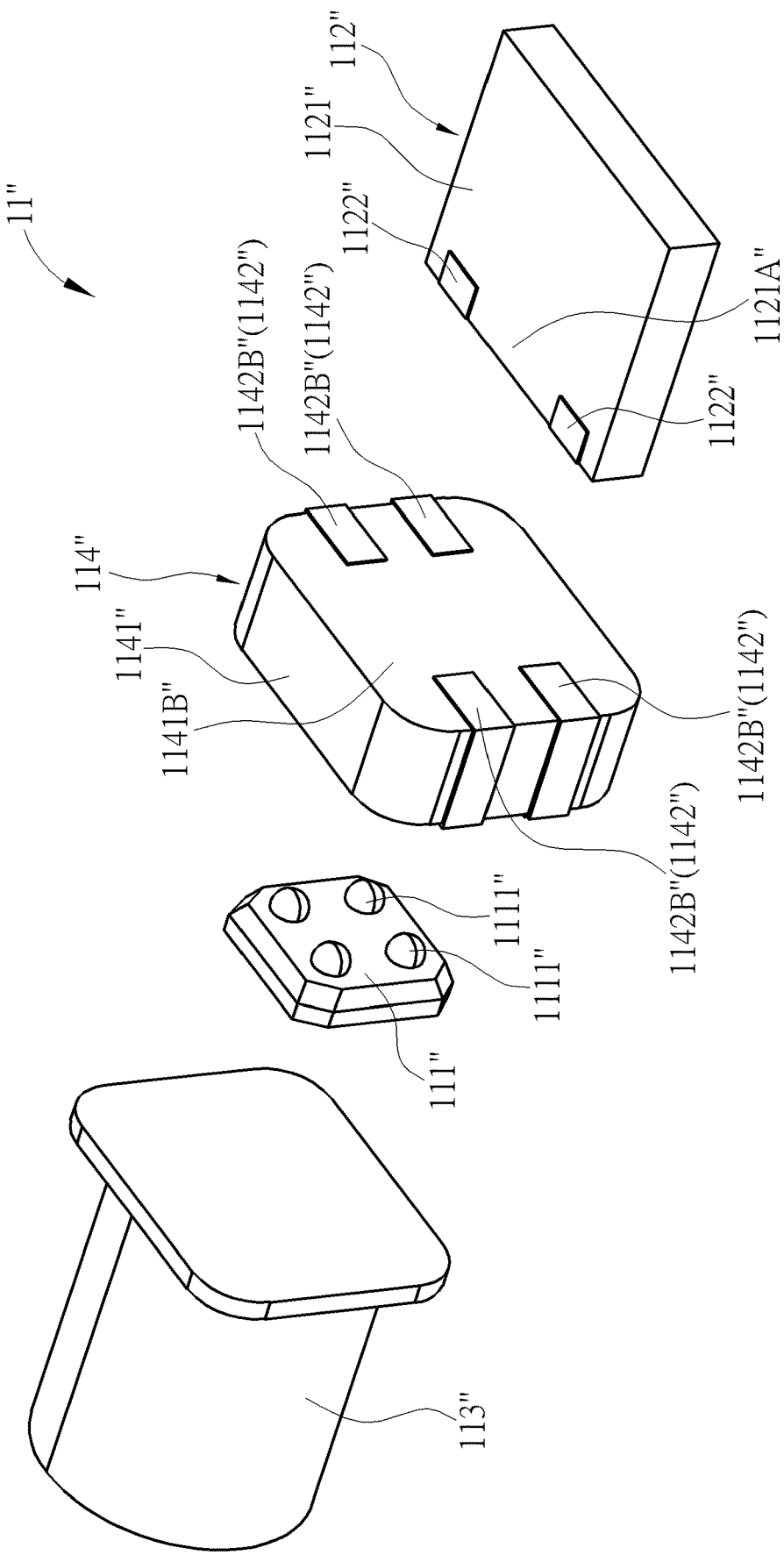

Please refer to FIG. 10 to FIG. 13. FIG. 10 and FIG. 11 are partial diagrams of an image capturing assembly 11" at different views according to a third embodiment of the present invention. FIG. 12 and FIG. 13 are partial exploded diagrams of the image capturing assembly 11" at different views according to the third embodiment of the present invention. The image capturing assembly 11" of this embodiment includes an image sensing device 111", a circuit board 112", a lens assembly 113", a fixture 114" and a passive electronic component 116".

As shown in FIG. 10 to FIG. 13, different from the second embodiment, a second portion 1142B" of each of first contacts 1142" of the fixture 114" is located at a second side 1141B" of a fixture body 1141" of the fixture 114" away from the lens assembly 113" and adjacent to a board body 1121" of the circuit board 112". There is no notch formed on the board body 1121", and the board body 1121" includes an abutting portion 1121A" abutting against the second side 1141B" of the fixture body 1141". In this embodiment, the abutting portion 1121A" is one of four side walls of the board body 1121".

The second portions 1142B" of two of the first contacts 1142" are located adjacent to a top side of the abutting portion 1121A" and arranged in a first arranging direction parallel to the circuit board 112" and the fixture 114" at an interval. The other two second portions 1142B" of the other two of the first contacts 1142" are located adjacent to a bottom side of the abutting portion 1121A" and arranged in the first arranging direction at an interval. Furthermore, along a direction perpendicular to the circuit board 112", the two second portions 1142B" located adjacent to the top side of the abutting portion 1121A" are spaced apart from and aligned with the other two second portions 1142B" located adjacent to the bottom side of the abutting portion 1121A" respectively, and an distance between the two corresponding second portions 1142B' along the direction perpendicular to the circuit board 112" is substantially equal to a thickness of the circuit board 112". Two of third contacts 1122" are disposed on the top side of the abutting portion 1121A" at an interval, and the other two of the third contacts 1122" are disposed on the bottom side of the abutting portion 1121A" at an interval. Furthermore, the two third contacts 1122" located adjacent disposed on the top side of the abutting portion 1121A" are aligned with the two third contacts 1122" disposed on the bottom side of the abutting portion 1121A" along the direction perpendicular to the circuit board 112", respectively. Each of the third contacts 1122" is affixed with and electrically connected to the corresponding second portion 1142B" of the corresponding first contact 1142" by a corresponding soldering structure, which is not shown in the figures. Other details of this embodiment are similar to the ones of the second embodiment. Detailed description is omitted herein for simplicity.

Figure 14:
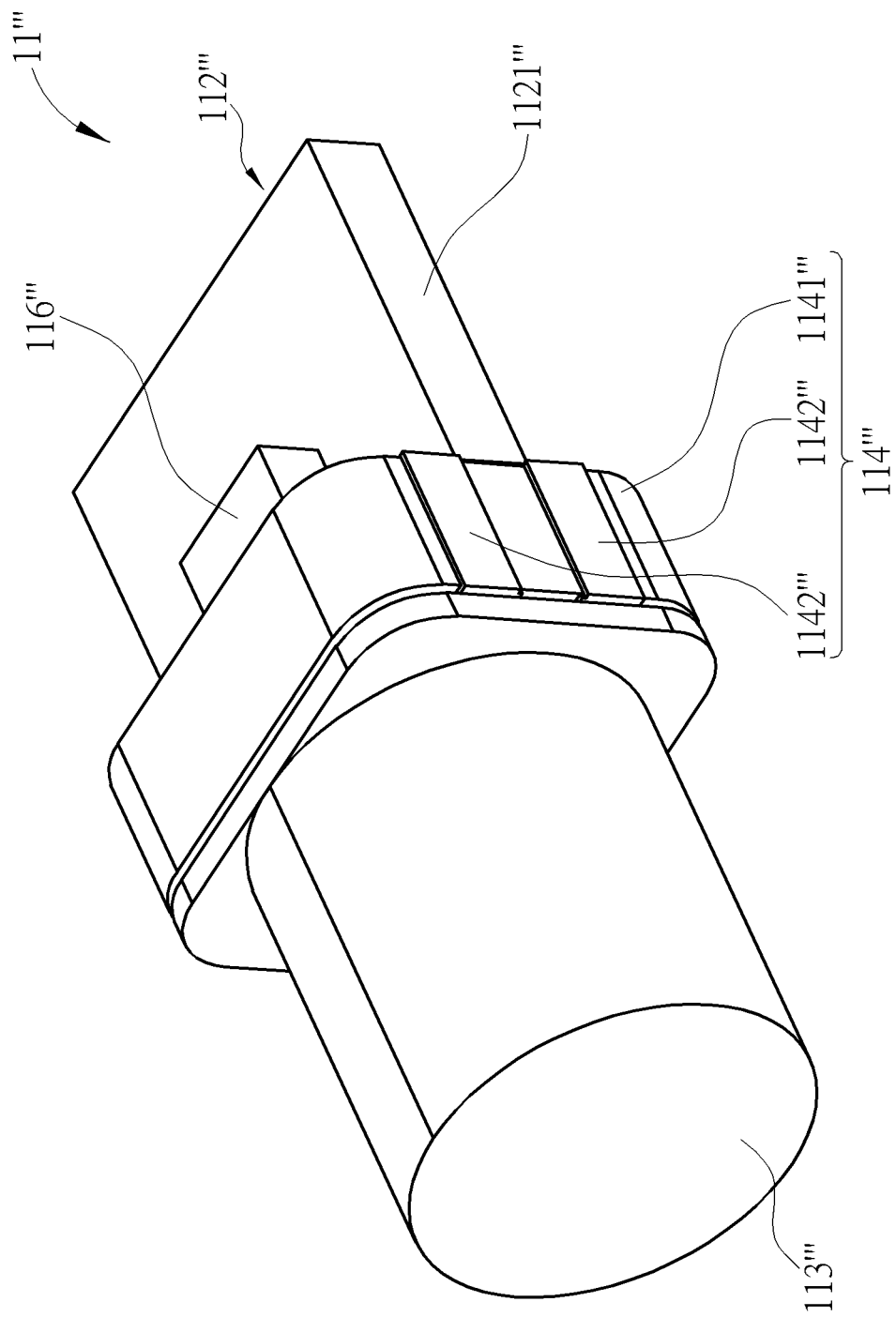
FIG. 14 and FIG. 15 are partial diagrams of an image capturing assembly at different views according to a fourth embodiment of the present invention.
Figure 15:
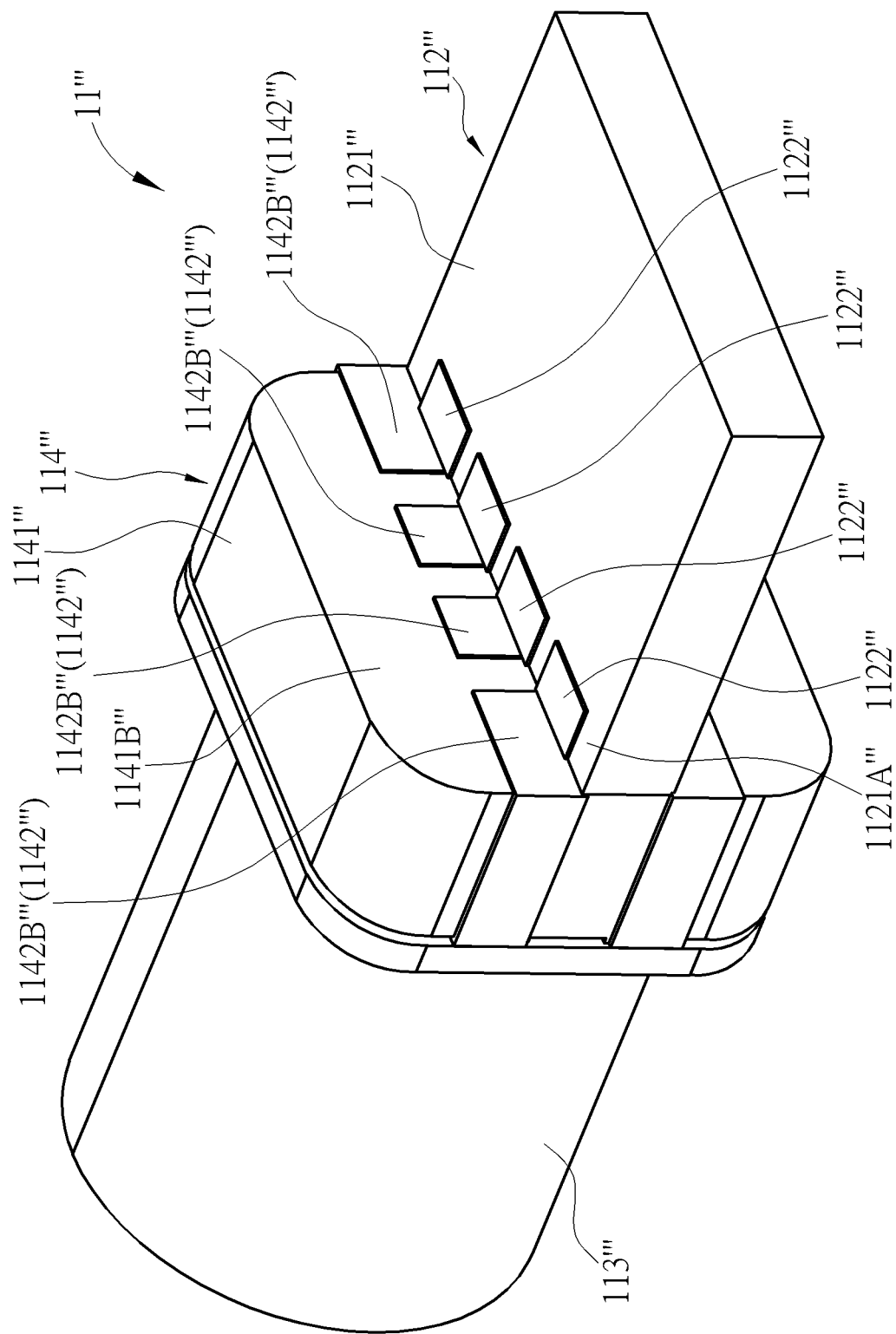
Figure 16:
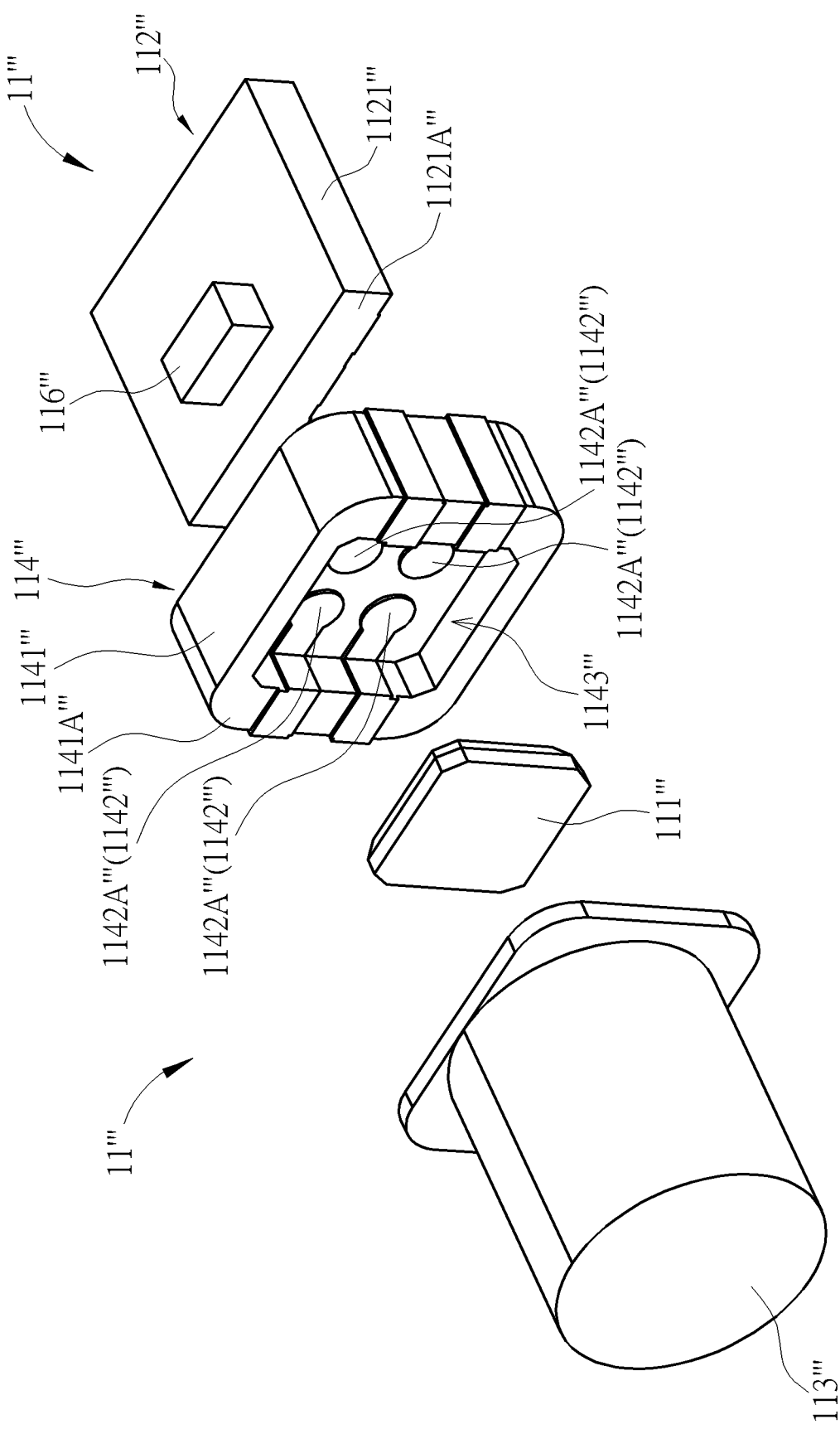
FIG. 16 and FIG. 17 are partial exploded diagrams of the image capturing assembly at different views according to the fourth embodiment of the present invention.
Figure 17:
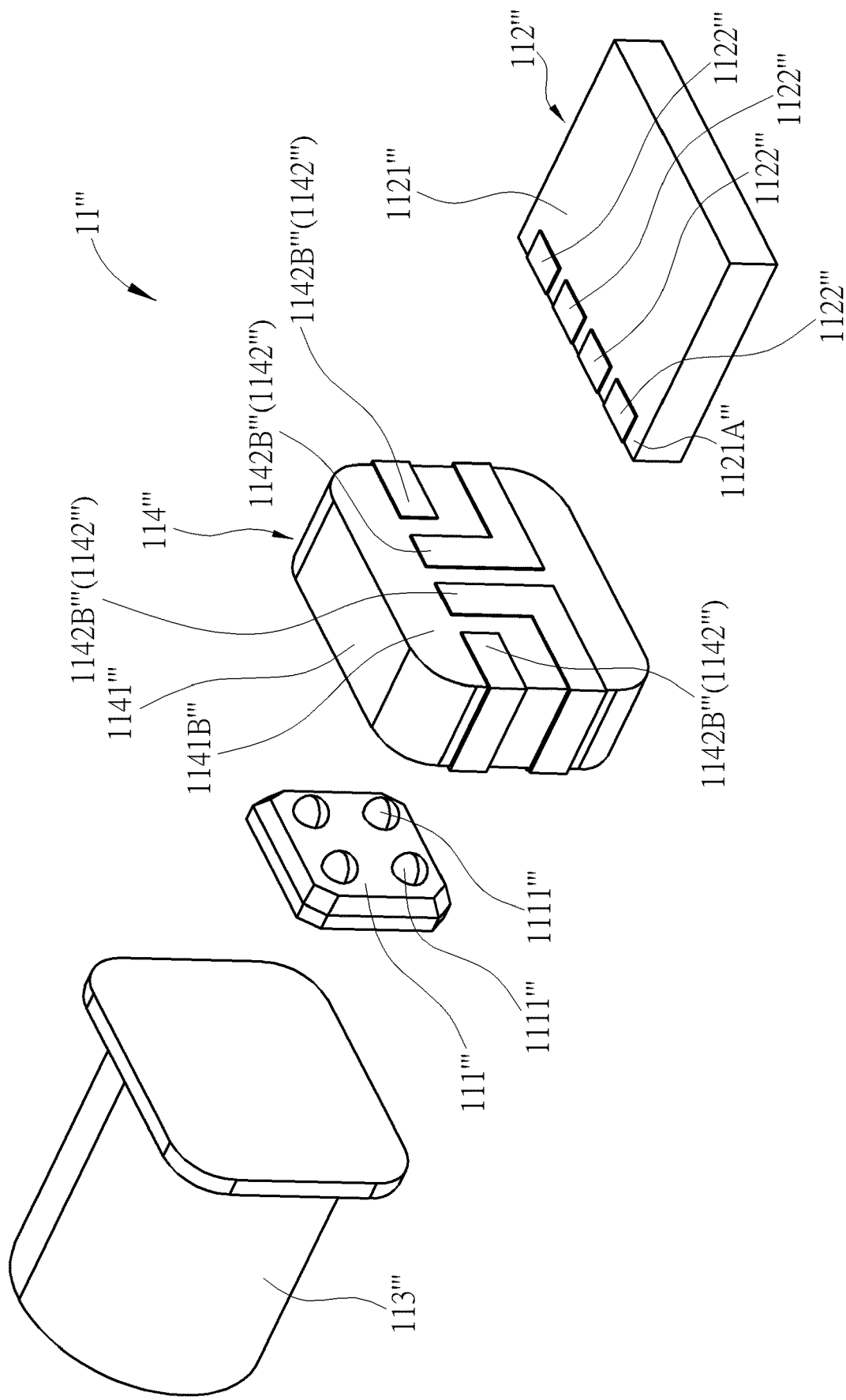

Please refer to FIG. 14 to FIG. 17. FIG. 14 and FIG. 15 are partial diagrams of an image capturing assembly 11''' at different views according to a fourth embodiment of the present invention. FIG. 16 and FIG. 17 are partial exploded diagrams of the image capturing assembly 11''' at different views according to the fourth embodiment of the present invention. The image capturing assembly 11''' of this embodiment includes an image sensing device 111''', a circuit board 112''', a lens assembly 113''', a fixture 114''' and a passive electronic component 116'''. A second portion 1142B''' of each of first contacts 1142''' of the fixture 114''' is located at a second side 1141B''' of a fixture body 1141''' of the fixture 114''' away from the lens assembly 113''' and adjacent to a board body 1121''' of the circuit board 112'''. There is no notch formed on the board body 1121" ', and the board body 1121" ' includes an abutting portion 1121A''' abutting against the second side 1141B''' of the fixture body 1141'''. In this embodiment, the abutting portion 1121A''' is one of four side walls of the board body 1121'''.

As shown in FIG. 14 to FIG. 17, different from the third embodiment, the second portions 1142B''' of all of the first contacts 1142''' are located adjacent to a top side of the abutting portion 1121A" ' and are arranged in a direction parallel to a second arranging direction parallel to the circuit board 112" ' and the fixture 114" ' at intervals. All of the third contacts 1122"' are disposed on the top side of the abutting portion 1121A''' and arranged in a direction parallel to the second arranging direction parallel to the circuit board 112''' and the fixture 114''' at intervals. Each of the third contacts 1122''' is affixed with and electrically connected to the second portion 1142B''' of the corresponding first contacts 1142''' by a corresponding soldering structure, which is not shown in the figures. Other details of this embodiment are similar to the ones of the third embodiment. Detailed description is omitted herein for simplicity.

Furthermore, the present invention is not limited to the aforementioned embodiments. In another embodiment, there can be two first contacts, two second contacts and two third contacts, wherein only one of the second contacts is electrically connected to a corresponding one of the third contacts by a corresponding one of the first contacts using one of the aforementioned configurations of the aforementioned embodiments, and the other of the second contacts is electrically connected to the other of the third contacts by the other of the first contacts using another configuration.

In contrast to the prior art, in the present invention, the fixture body of the fixture is perpendicular to and affixed with the board body of the circuit board. Furthermore, the image sensing device is disposed inside the accommodating space formed on the fixture body, and the second contact of the image sensing device is electrically connected to the third contact of circuit board by the first contact of the fixture. The aforementioned configuration of the present invention has a space-saving arrangement. Therefore, the present invention has advantages of compact structure and small size.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An image capturing assembly used in an endoscope, the image capturing assembly comprising:
    a fixture comprising:
        a fixture body comprising a first end surface, a second end surface opposite to the first end surface, and a peripheral surface located between and connected to the first end surface and the second end surface, an accommodating space being formed on one of the first end surface and the second end surface of the fixture body, the accommodating space being defined by a recess structure on the one of the first end surface and the second end surface of the fixture body; and
        at least one first contact disposed on the fixture body;
    a lens assembly having an optical axis and engaged with the first end surface of the fixture body along the optical axis;
    an image sensing device disposed inside the accommodating space, the image sensing device comprising at least one second contact electrically connected to the at least one first contact; and
    a circuit board comprising:
        a board body detachably engaged with the second end surface of the fixture body along the optical axis, and the board body comprising a side surface; and
        at least one third contact disposed on the side surface of the board body and electrically connected to the at least one first contact;
    wherein the first end surface and the second end surface of the fixture body are arranged in order along the optical axis, the first end surface engaged with the lens assembly is perpendicular to the optical axis, and the side surface of the board body is parallel to the optical axis.

2. The image capturing assembly of claim 1, wherein a notch is formed on the board body, and the fixture body is engaged with the notch.

3. The image capturing assembly of claim 2, wherein the at least one third contact is located adjacent to an outer periphery of the notch.

4. The image capturing assembly of claim 3, wherein the peripheral surface of the fixture body is parallel to the optical axis and perpendicular to the first end surface and the second end surface of the fixture body, the at least one first contact is a conducting trace extending from the first end surface to the second end surface through the peripheral surface and comprises a first portion and a second portion electrically connected to the first portion, the first portion is disposed on a wall of the fixture body formed on the first end surface and located adjacent to the accommodating space, the first portion is electrically connected to the at least one second contact, the second portion is disposed on a wall of the fixture body formed on the second end surface and located adjacent to the outer periphery of the notch, and the second portion is electrically connected to the at least one third contact.

5. The image capturing assembly of claim 1, wherein the image sensing device is positioned between the fixture body and the board body when the image sensing device is disposed inside the accommodating space.

6. The image capturing assembly of claim 5, wherein the accommodating space is formed on the second end surface of the fixture body.

7. The image capturing assembly of claim 1, wherein the image sensing device is positioned between the fixture body and the lens assembly when the image sensing device is disposed inside the accommodating space.

8. The image capturing assembly of claim 7, wherein the accommodating space is formed on the first end surface of the fixture body.

9. The image capturing assembly of claim 1, wherein an extending direction of the lens assembly is parallel to the optical axis, a normal direction of the first end surface of the fixture body and a normal direction of the second end surface of the fixture body, and the extending direction of the lens assembly is perpendicular to a normal direction of the side surface of the board body.

10. The image capturing assembly of claim 1, wherein the peripheral surface of the fixture body is parallel to the optical axis and perpendicular to the first end surface and the second end surface of the fixture body, the at least one first contact is a conducting trace extending from the first end surface to the second end surface through the peripheral surface and comprises a first portion and a second portion electrically connected to the first portion, the first portion is disposed on a wall of the fixture body formed on the first end surface and located adjacent to the accommodating space, the first portion is electrically connected to the at least one second contact, the second portion is disposed on a wall of the fixture body formed on the second end surface and located adjacent to the board body, and the second portion is electrically connected to the at least one third contact.

11. An endoscope comprising:
    an insertion tube; and
    an image capturing assembly connected to the insertion tube, the image capturing assembly comprising:
        a fixture comprising:
            a fixture body comprising a first end surface, a second end surface opposite to the first end surface, and a peripheral surface located between and connected to the first end surface and the second end surface, an accommodating space being formed on one of the first end surface and the second end surface of the fixture body, the accommodating space being defined by a recess structure on the one of the first end surface and the second end surface of the fixture body; and
            at least one first contact disposed on the fixture body;
        a lens assembly having an optical axis and engaged with the first end surface of the fixture body along the optical axis;
        an image sensing device disposed inside the accommodating space, the image sensing device comprising at least one second contact electrically connected to the at least one first contact; and
        a circuit board comprising:

a board body detachably engaged with the second end surface of the fixture body along the optical axis, and the board body comprising a side surface; and at least one third contact disposed on the side surface of the board body and electrically connected to the at least one first contact;

wherein the first end surface and the second end surface of the fixture body are arranged in order along the optical axis, the first end surface engaged with the lens assembly is perpendicular to the optical axis, and the side surface of the board body is parallel to the optical axis.

12. The endoscope of claim 11, wherein a notch is formed on the board body, and the fixture body is engaged with the notch.

13. The endoscope of claim 12, wherein the at least one third contact is located adjacent to an outer periphery of the notch.

14. The endoscope of claim 13, wherein the peripheral surface of the fixture body is parallel to the optical axis and perpendicular to the first end surface and the second end surface of the fixture body, the at least one first contact is a conducting trace extending from the first end surface to the second end surface through the peripheral surface and comprises a first portion and a second portion electrically connected to the first portion, the first portion is disposed on a wall of the fixture body formed on the first end surface and located adjacent to the accommodating space, the first portion is electrically connected to the at least one second contact, the second portion is disposed on a wall of the fixture body formed on the second end surface and located adjacent to the outer periphery of the notch, and the second portion is electrically connected to the at least one third contact.

15. The endoscope of claim 11, wherein the image sensing device is positioned between the fixture body and the board body when the image sensing device is disposed inside the accommodating space.

16. The endoscope of claim 15, wherein the accommodating space is formed on the second end surface of the fixture body.

17. The endoscope of claim 11, wherein the image sensing device is positioned between the fixture body and the lens assembly when the image sensing device is disposed inside the accommodating space.

18. The endoscope of claim 17, wherein the accommodating space is formed on the first end surface of the fixture body.

19. The endoscope of claim 11, wherein an extending direction of the lens assembly is parallel to the optical axis, a normal direction of the first end surface of the fixture body and a normal direction of the second end surface of the fixture body, and the extending direction of the lens assembly is perpendicular to a normal direction of the side surface of the board body.

20. The endoscope of claim 11, wherein the peripheral surface of the fixture body is parallel to the optical axis and perpendicular to the first end surface and the second end surface of the fixture body, the at least one first contact is a conducting trace extending from the first end surface to the second end surface through the peripheral surface and comprises a first portion and a second portion electrically connected to the first portion, the first portion is disposed on a wall of the fixture body formed on the first end surface and located adjacent to the accommodating space, the first portion is electrically connected to the at least one second contact, the second portion is disposed on a wall of the fixture body formed on the second end surface and located adjacent to the board body, and the second portion is electrically connected to the at least one third contact.

* * * * *